US012721806B2

(12) United States Patent
Florence et al.

(10) Patent No.: US 12,721,806 B2
(45) Date of Patent: Sep. 1, 2026

(54) COMBINATION OF PLANT EXTRACTS TO IMPROVE SKIN TONE

(71) Applicant: MARY KAY INC., Addison, TX (US)

(72) Inventors: Tiffany Florence, Dallas, TX (US); David Gan, Southlake, TX (US); Michelle Hines, Hickory Creek, TX (US)

(73) Assignee: MARY KAY INC., Addison, TX (US)

( * ) Notice: Subject to any disclaimer, the term of this patent is extended or adjusted under 35 U.S.C. 154(b) by 176 days.

(21) Appl. No.: 18/517,518

(22) Filed: Nov. 22, 2023

(65) Prior Publication Data

US 2024/0165012 A1 May 23, 2024

Related U.S. Application Data

(60) Continuation of application No. 16/998,820, filed on Aug. 20, 2020, now Pat. No. 11,865,202, which is a continuation of application No. 15/828,694, filed on Dec. 1, 2017, now Pat. No. 10,780,041, which is a continuation of application No. 14/827,835, filed on Aug. 17, 2015, now Pat. No. 9,861,573, which is a division of application No. 13/720,557, filed on Dec. 19, 2012, now Pat. No. 9,138,401.

(60) Provisional application No. 61/577,462, filed on Dec. 19, 2011.

(51) Int. Cl.

| | |
|---|---|
| ***A61K 36/00*** | (2006.01) |
| ***A61K 8/49*** | (2006.01) |
| ***A61K 8/97*** | (2017.01) |
| ***A61K 8/9789*** | (2017.01) |
| ***A61K 36/48*** | (2006.01) |
| ***A61P 17/00*** | (2006.01) |
| ***A61Q 19/00*** | (2006.01) |
| ***A61Q 19/02*** | (2006.01) |

(52) U.S. Cl.

CPC .............. *A61K 8/97* (2013.01); *A61K 8/4926* (2013.01); *A61K 8/9789* (2017.08); *A61K 36/48* (2013.01); *A61P 17/00* (2018.01); *A61Q 19/00* (2013.01); *A61Q 19/02* (2013.01); *A61K 2800/30* (2013.01); *A61K 2800/5922* (2013.01)

(58) Field of Classification Search

CPC ..................................................... A61Q 19/02

See application file for complete search history.

(56) References Cited

U.S. PATENT DOCUMENTS

| | | | |
|---|---|---|---|
| 2,798,053 | A | 7/1957 | Brown |
| 3,755,560 | A | 8/1973 | Dickert et al. |
| 4,421,769 | A | 12/1983 | Dixon et al. |
| 4,509,949 | A | 4/1985 | Huang et al. |
| 4,599,379 | A | 7/1986 | Flesher et al. |
| 4,628,078 | A | 12/1986 | Glover et al. |
| 4,835,206 | A | 5/1989 | Farrar et al. |
| 4,849,484 | A | 7/1989 | Heard |
| 5,011,681 | A | 4/1991 | Ciotti et al. |
| 5,087,445 | A | 2/1992 | Haffey et al. |
| 5,100,660 | A | 3/1992 | Hawe et al. |
| 5,411,741 | A | 5/1995 | Zaias |
| 5,639,460 | A | 6/1997 | Raymond |
| 5,939,082 | A | 8/1999 | Oblong et al. |
| 6,197,343 | B1 | 3/2001 | Minami et al. |
| 6,528,490 | B2 | 3/2003 | Steck |
| 6,641,848 | B1 | 11/2003 | Bonte et al. |
| 6,863,897 | B2 | 3/2005 | Love et al. |
| 8,063,005 | B2 | 11/2011 | Kalidindi |
| 8,236,288 | B2 | 8/2012 | Mehta et al. |
| 8,247,405 | B2 | 8/2012 | Madison |
| 8,440,237 | B2 | 5/2013 | Hines et al. |
| 8,481,090 | B2 | 7/2013 | Hines et al. |
| 8,747,926 | B2 | 6/2014 | Hines et al. |
| 9,561,198 | B2 | 2/2017 | Hines et al. |
| 9,849,077 | B2 | 12/2017 | Gan et al. |
| 2001/0033850 | A1 | 10/2001 | Vatter et al. |
| 2003/0035817 | A1 | 2/2003 | Ito et al. |
| 2003/0049212 | A1 | 3/2003 | Robinson et al. |
| 2003/0170319 | A1 | 9/2003 | Netke et al. |
| 2003/0224064 | A1 | 12/2003 | Kling |
| 2004/0161524 | A1 | 8/2004 | Sakai et al. |
| 2004/0166069 | A1 | 8/2004 | Gupta |
| 2005/0019283 | A1 | 1/2005 | Nonaka et al. |
| 2005/0080160 | A1 | 4/2005 | Seabrook et al. |
| 2005/0129780 | A1 | 6/2005 | Holcomb-Halstead et al. |
| 2006/0008538 | A1 | 1/2006 | Wu et al. |
| 2006/0018867 | A1 | 1/2006 | Kawasaki et al. |
| 2006/0165636 | A1 | 7/2006 | Hasebe et al. |
| 2006/0165644 | A1 | 7/2006 | Tanaka et al. |

(Continued)

FOREIGN PATENT DOCUMENTS

| | | |
|---|---|---|
| CA | 2386648 | 11/2003 |
| CN | 1165012 | 11/1997 |

(Continued)

OTHER PUBLICATIONS

"Bluenikko Tonymoly Floria Whitening Capsule Essence", 2012. pp. 1-3. <http://www.cosdna.com/chs/cosmetic_8>.

(Continued)

*Primary Examiner* — Qiuwen Mi

(74) *Attorney, Agent, or Firm* — NORTON ROSE FULBRIGHT US LLP

(57) ABSTRACT

A method of whitening skin or evening out skin tone is disclosed. The method can include topically applying to skin in need of treatment a composition comprising *Cocos nucifera* extract and an effective amount of an extract of azuki bean, wherein topical application of the composition whitens skin or evens out skin tone.

20 Claims, No Drawings

(56) References Cited

U.S. PATENT DOCUMENTS

| | | | |
|---|---|---|---|
| 2006/0182708 | A1 | 8/2006 | Bockmuhl et al. |
| 2006/0216254 | A1 | 9/2006 | Majmudar et al. |
| 2006/0233845 | A1 | 10/2006 | Lukowski et al. |
| 2007/0122492 | A1 | 5/2007 | Behr et al. |
| 2007/0248633 | A1 | 10/2007 | Baldo |
| 2007/0297999 | A1 | 12/2007 | Fonolla Moreno et al. |
| 2008/0008673 | A1 | 1/2008 | Willemin et al. |
| 2008/0058281 | A1 | 3/2008 | Yates et al. |
| 2008/0305059 | A1 | 12/2008 | Chaudhuri |
| 2009/0042846 | A1 | 2/2009 | Gupta |
| 2009/0253663 | A1 | 10/2009 | Akamatsu et al. |
| 2009/0263516 | A1 | 10/2009 | Cyr |
| 2009/0324661 | A1 | 12/2009 | Polonka et al. |
| 2010/0068318 | A1 | 3/2010 | Miljkovic |
| 2010/0136145 | A1 | 6/2010 | Bombardelli et al. |
| 2010/0189669 | A1 | 7/2010 | Hakozaki et al. |
| 2010/0203077 | A1 | 8/2010 | Schnittger et al. |
| 2010/0303854 | A1 | 12/2010 | Hines et al. |
| 2011/0081305 | A1 | 4/2011 | Cochran et al. |
| 2011/0082217 | A1 | 4/2011 | Johnson et al. |
| 2011/0086060 | A1 | 4/2011 | Bidamant et al. |
| 2011/0117227 | A1 | 5/2011 | Lee et al. |
| 2011/0142972 | A1 | 6/2011 | Kirn et al. |
| 2011/0243983 | A1 | 10/2011 | Paufique |
| 2012/0002669 | A1 | 1/2012 | Dietterle et al. |
| 2012/0058140 | A1 | 3/2012 | Ceccoli et al. |
| 2012/0087878 | A1 | 4/2012 | Hines et al. |
| 2012/0128605 | A1 | 5/2012 | Cochran et al. |
| 2012/0128613 | A1 | 5/2012 | Cochran et al. |
| 2012/0164121 | A1 | 6/2012 | Paufique |
| 2012/0189684 | A1 | 7/2012 | Buckley et al. |
| 2012/0237460 | A1 | 9/2012 | Swanson et al. |
| 2012/0283226 | A1 | 11/2012 | Buckley et al. |
| 2012/0288478 | A1 | 11/2012 | Florence et al. |
| 2013/0071426 | A1 | 3/2013 | Serra-Baldrich et al. |
| 2013/0156873 | A1 | 6/2013 | Florence et al. |
| 2013/0195925 | A1 | 8/2013 | Arshed |
| 2013/0237460 | A1 | 9/2013 | Deierling et al. |
| 2018/0071203 | A1 | 3/2018 | Gan et al. |
| 2019/0151387 | A1 | 5/2019 | Hines et al. |

FOREIGN PATENT DOCUMENTS

| | | |
|---|---|---|
| CN | 1627956 | 2/2003 |
| CN | 1190232 | 2/2005 |
| CN | 1713889 | 12/2005 |
| CN | 1883449 | 6/2006 |
| CN | 1840117 | 10/2006 |
| CN | 1960700 | 5/2007 |
| CN | 1960743 | 5/2007 |
| CN | 101904804 | 12/2010 |
| CN | 102028626 | 4/2011 |
| CN | 102188331 | 9/2011 |
| CN | 102300551 | 12/2011 |
| CN | 102366375 | 3/2012 |
| DE | 102 51 709 | 2/2004 |
| DE | 10 2005 025 156 | 6/2005 |
| DE | 10 2005 028 386 | 6/2005 |
| DE | 103 20 603 | 6/2005 |
| DE | 103 33 245 | 7/2005 |
| DE | 10 2004 011 968 | 9/2005 |
| DE | B 198 49 107 | 6/2006 |
| DE | 10 2005 063 063 | 10/2006 |
| DE | 20 2007 002 978 | 2/2007 |
| DE | 10 2006 054 621 | 5/2007 |
| DE | 20 2007 008 601 | 6/2007 |
| EP | 0 641 557 | 3/1995 |
| EP | 0 692 257 | 1/1996 |
| EP | 0 826 372 | 3/1998 |
| EP | 1 029 531 | 2/1999 |
| EP | 0915693 | 5/1999 |
| EP | B 1 027 064 | 8/2000 |
| EP | 1 194 111 | 4/2002 |
| EP | 1 200 317 | 4/2002 |
| EP | 1 407 879 | 5/2002 |
| EP | 1 283 713 | 2/2003 |
| EP | 1 455 722 | 9/2004 |
| EP | A 1 466 589 | 10/2004 |
| EP | B 1 493 421 | 1/2005 |
| EP | 1 602 354 | 12/2005 |
| EP | 1 708 677 | 10/2006 |
| EP | 1 813 252 | 12/2006 |
| EP | A 1 728 519 | 12/2006 |
| EP | 1 759 688 | 3/2007 |
| EP | 1967198 | 5/2009 |
| EP | 2316411 | 5/2011 |
| EP | 2522330 | 11/2015 |
| FR | 2942136 | 8/2010 |
| JP | 359013707 | 1/1984 |
| JP | H1029911 | 2/1998 |
| JP | 2002265343 | 9/2002 |
| JP | 2006176481 | 7/2006 |
| JP | 2007210915 | 8/2007 |
| KR | 10-2001-0000479 | 1/2001 |
| KR | 10-1997-0067591 | 4/2001 |
| KR | 1020020080657 | 10/2001 |
| KR | 2001-110001 | 12/2001 |
| KR | 0357824 | 10/2002 |
| KR | 10-2003-0089710 | 11/2003 |
| KR | 10-0443588 | 8/2004 |
| KR | 10-2004-7011038 | 9/2004 |
| KR | 10-0512690 | 9/2005 |
| KR | 10-0525842 | 10/2005 |
| KR | 10-2003-0044506 | 11/2005 |
| KR | 10-2006-0106310 | 10/2006 |
| KR | 0841072 | 6/2008 |
| KR | 1020080070334 | 7/2008 |
| KR | 10-2010-0021088 | 2/2010 |
| KR | 20100055099 | 5/2010 |
| KR | 1020100090530 | 8/2010 |
| KR | 1020110036687 | 4/2011 |
| KR | 10-2011-0117376 | 10/2011 |
| KR | 1020120001597 | 1/2012 |
| KR | 1020120058724 | 6/2012 |
| KR | 1020120068224 | 6/2012 |
| KR | 1020120091719 | 8/2012 |
| KR | 1020120092283 | 8/2012 |
| KR | 20150007464 | 1/2015 |
| KR | 20160007956 | 1/2016 |
| KR | 20180064269 | 6/2018 |
| KR | 20200041130 | 4/2020 |
| WO | WO 1998/052533 | 11/1998 |
| WO | WO 01/68576 | 9/2001 |
| WO | WO 02/085965 | 3/2002 |
| WO | WO 02/089758 | 11/2002 |
| WO | WO 03/070152 | 2/2003 |
| WO | WO 03/075862 | 3/2003 |
| WO | WO 03/099244 | 12/2003 |
| WO | WO 04/066912 | 2/2004 |
| WO | WO 04/093840 | 2/2004 |
| WO | WO 04/078189 | 3/2004 |
| WO | WO 04/045575 | 6/2004 |
| WO | WO 04/050108 | 6/2004 |
| WO | WO 04/105737 | 12/2004 |
| WO | WO 2005/004833 | 1/2005 |
| WO | WO 05/011716 | 2/2005 |
| WO | WO 05/095959 | 3/2005 |
| WO | WO 2005/044214 | 5/2005 |
| WO | WO 2005/067885 | 7/2005 |
| WO | WO 05/075623 | 8/2005 |
| WO | WO 2005/094770 | 10/2005 |
| WO | WO 06/032143 | 3/2006 |
| WO | WO 06/051246 | 5/2006 |
| WO | WO 06/053415 | 5/2006 |
| WO | WO 06/067945 | 6/2006 |
| WO | WO 06/068759 | 6/2006 |
| WO | WO 06/128032 | 11/2006 |
| WO | WO 2006/117055 | 11/2006 |
| WO | WO 07/007287 | 1/2007 |
| WO | WO 07/007288 | 1/2007 |
| WO | WO 07/007290 | 1/2007 |
| WO | WO 07/007291 | 1/2007 |
| WO | WO 07/007292 | 1/2007 |
| WO | WO 07/007293 | 1/2007 |

(56) References Cited

FOREIGN PATENT DOCUMENTS

| | | |
|---|---|---|
| WO | WO 07/007296 | 1/2007 |
| WO | WO 07/016223 | 2/2007 |
| WO | WO 07/044945 | 4/2007 |
| WO | WO 07/077292 | 7/2007 |
| WO | WO 07/085902 | 8/2007 |
| WO | WO 2007/106501 | 9/2007 |
| WO | WO 07/113830 | 10/2007 |
| WO | WO 07/116147 | 10/2007 |
| WO | WO 07/122422 | 11/2007 |
| WO | WO 07/146816 | 12/2007 |
| WO | WO 08/032212 | 3/2008 |
| WO | WO 08/034702 | 3/2008 |
| WO | WO 08/034703 | 3/2008 |
| WO | WO 08/042331 | 4/2008 |
| WO | WO 2010/000587 | 1/2010 |
| WO | WO 2010/003806 | 1/2010 |
| WO | WO 2010/064878 | 6/2010 |
| WO | WO 2010/115472 | 10/2010 |
| WO | WO 2012/002669 | 1/2012 |
| WO | WO 2012/011908 | 1/2012 |
| WO | WO 2013/046137 | 4/2013 |

OTHER PUBLICATIONS

"Abundance of Nature in Town's Reach," The Journal, May 1, 1999, Executive Motoring, p. 47.

"Garden Showcases Unique Plant Collection," Calgary Herold, Jun. 23, 1999, Gardens, VS16.

"Kosmetika Velocity Mary Kay"; Online, URL<http://www.ugrei.net/forum/Kosmetika-Velocity-Mary-t12660.html&st=40> 6 pages accessed Dec. 17, 2012.

"Mary Kay Anti-Acne Series Products" Jan. 15, 2009, Accessed from the Internet URL < http://www.cunan.com/knowledge/1687.html >.

"Module One: Nature's Pain Relieving Substances," Aspirin Alternatives: The Top Natural Pain-Relieving Analgesics, Jun. 1, 1999, p. 52.

"The Skin Care Market," Household and Personal Products Industry, May 1, 2001, No. 5, vol. 38, p. 112.

Begoun, Paula, *Don't go to the Cosmetic Counter Without Me*. New World Press, 2009, 881. (Counterpart English Publication).

Collantes et al., "Azuki bean (*Vigna angularis*) extract inhibits the development of experimentally induced atopic dermatitis-like skin lesions in NC/Nga mice" *Food Chemistry* 2011, 132, 1269-1275.

Database GNPD [Online] MINTEL; Dec. 2013 (Dec. 2013), "Whitening & Multieffect B.B Cream with Edelweiss" , XP002740353, Database accession No. 2271200.

Database GNPD [Online] MINTEL; Sep. 2011 (Sep. 2011), "Whitening Essence", XP002740354, Database accession No. 1625153.

De Smet, "Herbal Remedies" New England Journal of Medicine 2002; 347(25): 2046-56.

Extended European Search Report issued in European Patent Application No. 19/181,364 .1, issued Aug. 8, 2019.

Extended European Search Report Issued in European Patent Application No. 12860455, dated Sep. 21, 2015.

Gottschalck, et al., "*Phaseolus vulgaris* (Kidney Bean) Seed Extract," International Cosmetic Ingredient Dictionary and Handbook, 13th Ed., vol. 2, Personal Care Products Council, p. 2228, 2010.

In the yard, The Desert Sun; Aug. 5, 2006, p. 3F.

International Cosmetic Ingredient Dictionary and Handbook, $12^{th}$ Edition, 2008, vol. 2, p. 1449.

International Cosmetic Ingredient Dictionary and Handbook, $12^{th}$ Edition, 2008, vol. 2, p. 1651-1652.

International Cosmetic Ingredient Dictionary and Handbook, $12^{th}$ Edition, 2008, vol. 1, p. 1158.

International Cosmetic Ingredient Dictionary and Handbook, $12^{th}$ Edition, 2008, vol. 2, p. 2034.

International Cosmetic Ingredient Dictionary and Handbook, $12^{th}$ Edition, 2008, vol. 1, p. 280.

International Cosmetic Ingredient Dictionary and Handbook, $12^{th}$ Edition, 2008, vol. 1, p. 84.

International Cosmetic Ingredient Dictionary and Handbook, $12^{th}$ Edition, 2008, vol. 2, p. 1731.

Ke, Rui "Resorcinol Derivatives—A Highly Efficient Lightening Component Will Become Popular," 2012, p. 3, <http://www.truebuty.com/whitenins-insredient-res.html>.

Kovacevic, Katarina. "Kelp from the Sea," 2013. <URL:http://www.americanspa.com/americanspa/spa-treatments/kelp-sea-0 >.

Li, Yong, "Peptide Clinical Nutrition," Peking University Medical Press, 2012, p. 324. (English Translation of Relevant Section).

Liu, Liping "The Foundation of Practical Beauty Medicines" Chonqing University Press, 2012, p. 84. (English Translation of Relevant Section).

MacDonald, "Natural Ingredients in Personal Care Products." Retrieved from the Internet on Jan. 16, 2016, <URL: http://www.happi.com/issued/2001-06/view_features/natural-ingredients-in-personal-care-products/ >.

Office Action issued in Corresponding Chinese Patent Application No. 201510102126, dated May 14, 2019 (English Translation).

Phillipson, "New Drugs from Nature—It Could be Yew," Phytotherapy Research, 13:1999, 2-8.

Pulse Canada—"Bean (*Phaseolus vulgaris*)," Retrieved on Oct. 12, 2016. Retrieved from internet <URL: http://www.pulsecanada.com/about-us/what-is-a-pulse/bean >.

Revilla et al., "Comparison of Several Procedures Used for the Extraction of Anthocyanins from Red Grapes," J. Agric. Food Chem. 1998; 46: 4592-4597.

Tsuda et al., "Inhibition of Tyrosinase Activity by the Anthocyanin Pigments Isolated from Phaseolus vulgaris L." *Food Sci. Technol. Int. Tokyo*, 3(1): 1997, 82-83.

Wang et al., "Development and Application of Cosmetic Plant Additives (Version 1)" *China Light Industry Press*, 2013, 326-327. (English Translation).

Wang, Jianxin et al. *The Encyclopedia of Raw Plant Materials of Cosmetics*, China Textile & Apparel Press, 2012, 401-402 (English Translation).

Wang, Jianxin et al., *The Encyclopedia of Cosmetics and Plant Raw Materials*, China Textile & Apparel Press, 2012, 12-13. (English Translation).

Winsome flowering veins; New Straits Times, Feb. 23, 2002, p. 8.

COMBINATION OF PLANT EXTRACTS TO IMPROVE SKIN TONE

CROSS REFERENCE TO RELATED APPLICATIONS

This application is a continuation of U.S. application Ser. No. 16/998,820 filed Aug. 20, 2020, which is a continuation of U.S. application Ser. No. 15/828,694 filed Dec. 1, 2017 (now U.S. Pat. No. 10,780,041), which is a continuation of U.S. application Ser. No. 14/827,835 filed Aug. 17, 2015 (now U.S. Pat. No. 9,861,573, which is a divisional of U.S. application Ser. No. 13/720,557 filed Dec. 19, 2012 (now U.S. Pat. No. 9,138,401), which claims the benefit of U.S. Provisional Application 61/577,462 filed Dec. 19, 2011. The contents of the referenced applications are incorporated into the present application by reference.

BACKGROUND OF THE INVENTION

A. Field of the Invention

The present invention relates generally to compositions that can be used to improve the skin's visual appearance. For instance, the present invention concerns topical skin care compositions that include azuki bean navy bean or extracts thereof or a combination of both. In certain aspects, the compositions can be used to lighten skin, even out skin color, or treat hyperpigmentation.

B. Description of Related Art

Coloring in human skin is caused by melanin. Melanin is produced in special dendritic cells, melanocytes, which are found below or between the basal cells of the epidermis of the skin (U.S. Pat. No. 5,411,741). Melanin is synthesized by a reaction cascade triggered by the enzyme tyrosinase (U.S. Pat. No. 5,262,153).

Typical pigmentation is characterized by an even, uniform coloration of the skin. Many individuals have excess melanin pigmentation or a hyperpigmentation patch which can cause pigmentary variation or abnormal pigmentation of the skin. This may lead to unwanted freckles or dark spots such as senile lentigo, liver spots, melasma, brown or age spots, vitiligo, sunburn pigmentation, post-inflammatory hyperpigmentation due to abrasion, burns, wounds or dermatitis, phototoxic reaction and other similar small, fixed pigmented lesions. It is often desirable to lighten these areas or even out the appearance of irregularly pigmented areas of skin. Individuals may also wish to increase fairness or reduce the overall level of pigmentation in the skin. In either case, the hyperpigmentation is usually viewed as cosmetically undesirable and individuals often wish to lighten the skin.

There are known chemical compounds that can whiten/lighten skin. One such compound is hydroquinone. This compound, however, has been known to have skin irritating properties. Others have also attempted to create natural formulations for whitening skin. For instance, Korean Publication 10-2005-0028920 discloses the use of a rinse-off soap to wash and whitening skin. The soap includes mung beans, brown rice, adlay, white corvania (baektae) (i.e., soybean or *Glycine max* L. Merr), dried *Artemisia* leaves, dried peach seeds, silkworms killed by white muscardine disease, sangyak, *Houttuynia cordata*, dried dodder seeds, orange peels, green tea leaves, sea mustard, kelp, and buckwheat. Such a composition, however, relies on a multitude of ingredients to achieve its desired effect.

SUMMARY OF THE INVENTION

The present invention overcomes deficiencies in the art by providing an effective and natural alternative to lighten skin, reduce the appearance of uneven skin tone, and/or treat melasmic skin. The compositions of the present invention utilize natural plants or aqueous extracts of said natural plants or combinations thereof to achieve these effects. The natural plants can be from the azuki bean and/or from the navy bean, both of which are described in further detail throughout this specification. This results in a natural and effective way to lighten or whiten skin by using natural plant products or water-based liquid extracts, while reducing or eliminating the need to use other whitening agents such as caustic chemicals (e.g., hydroquinone, ascorbyl acid 2-glucoside, magnesium ascorbyl phosphate, niacinamide, creatinine, undecylenoyl phenylalanine, etc.).

In one instance, there is disclosed a method of whitening skin or evening out skin tone, comprising topically applying to skin in need of treatment a composition comprising dried navy (haricot)-bean (*Phaseolus vulgaris*) powder or an aqueous extract thereof, wherein topical application of the composition whitens skin or evens out skin tone. The composition can include dried navy (haricot)-bean (*Phaseolus vulgaris*) powder or an aqueous extract of dried navy (haricot)-bean (*Phaseolus vulgaris*) powder or a combination of both. The composition can be applied to skin identified as having hyperpigmentation, melasmic skin, sun spots, aged spots, discolored spots, skin having uneven skin tone, etc. The composition can further include azuki bean or an extract thereof such as an aqueous extract or an alcoholic extract or an aqueous/alcoholic extract. The composition can be formulated as an emulsion, gel, serum, lotion, cream, ointment, etc. The composition can remain on the skin for at least 1, 2, 3, 4, 5, 6, 7, 8, 9, 10, 20, 30 minutes, 1, 2, 3, 4, 5, 6, 7, 8, 9, 10, 11, 12, or 24 hours. The composition can be removed from the skin with water or soap. In certain aspects, the composition does not include known skin whitening agents such as hydroquinone, ascorbyl acid 2-glucoside, magnesium ascorbyl phosphate, niacinamide, creatinine, undecylenoyl phenylalanine, etc. In certain aspects, the composition does not include beans or extracts thereof other than the aforementioned navy bean and azuki bean (e.g., soybean, mung bean, black turtle beans, cranberry and borlotti beans, flageolet beans, green or yellow pea beans, pink beans, red beans, kidney beans, pinto beans, yellow beans, etc.). In some instance, the composition does not include an ecdysteroid (e.g., β-ecdysone, acylated β-ecdysone, and/or ecdysterone). In some instances, the composition does not include a flour or a flour phase. The composition can include 1 to 5% w/w of dried navy (haricot)-bean (*Phaseolus vulgaris*) powder or azuki bean or an aqueous extract thereof or 0.001, 0.01, 0.1, 1, 2, 3, 4, 5, 6, 7, 8, 9, 10, 11, 12, 13, 14, 15, 16, 17, 18, 19, or 20% or more. The composition can include a UV absorption agent. In some instances, the compositions of the present invention can be used reduce effective reduction in tyrosinase activity and melanogenesis activity can be obtained with relatively low concentrations of azuki bean and/or navy bean or extracts thereof.

In certain embodiments, the compositions are formulated into topical skin care compositions. The compositions can be cosmetic compositions. In other aspects, the compositions can be included in a cosmetic vehicle. Non-limiting examples of cosmetic vehicles are disclosed in other sections of this specification and are known to those of skill in the art. Examples of cosmetic vehicles include emulsions (e.g., oil-in-water and water-in-oil emulsions), creams, lotions, solutions (e.g., aqueous or hydro-alcoholic solutions), anhydrous bases (e.g., lipstick or a powder), gels, and ointments. In other non-limiting embodiments, the compositions of the present invention can be included in anti-aging, skin-whitening/lightening, cleansing, or moisturizing products. The compositions can also be formulated for topical skin application at least 1, 2, 3, 4, 5, 6, 7, or more times a day during use. In other aspects of the present invention, compositions can be storage stable or color stable, or both. It is also contemplated that the viscosity of the composition can be selected to achieve a desired result (e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000 cps, etc., as measured on a Brookfield Viscometer using a TC spindle at 2.5 rpm at 25° C.). In particular embodiments, the composition has a viscosity ranging from 14,000 to 30,000 cps. The compositions in non-limiting aspects can have a pH of about 6 to about 9. In other aspects, the pH can be 1, 2, 3, 4, 5, 6, 7, 8, 9, 10, 11, 12, 13, or 14. In other aspects, the compositions can be sunscreens having a sun protection factor (SPF) of 1, 5, 10, 15, 20, 25, 30, 35, 40, 45, 50, 55, or more.

In particular aspects, the compositions can be oil-free, substantially anhydrous, and/or anhydrous. Other aspects include compositions having water.

The compositions of the present invention can also be modified to have a desired oxygen radical absorbance capacity (ORAC) value. In certain non-limiting aspects, the compositions of the present invention can be modified to have an ORAC value per mg of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, 95, 100, 200, 300, 400, 500, 600, 700, 800, 900, 1000, 2000, 3000, 4000, 5000, 6000, 7000, 8000, 9000, 10000, 15000, 20000, 30000, 50000, 100000 or more or any range derivable therein.

In other non-limiting aspects of the present invention, the compositions can further include a vitamin, a mineral, an essential fatty acid, an amino acid, a flavonoid, and/or a protein, or a combination thereof. Non-limiting examples of vitamins include the B vitamins (e.g., B1, B2, B6, B12, niacin, folic acid, biotin, and pantothenic acid), vitamin C, vitamin D, vitamin E (e.g., tocopherol or tocopheryl acetate), vitamin A (e.g., palmitate, retinyl palmitate, or retinoic acid), and vitamin K. Non-limiting examples of minerals include iron, potassium, phosphorus, magnesium, manganese, selenium, and calcium. Non-limiting examples of essential fatty acids include Omega 3 (linolenic acid), Omega 6 (linoleic acid) and Omega 9 (oleic acid) essential fatty acid, or a combination thereof. Non-limiting examples of amino acids include essential amino acids (e.g., lysine, leucine, isoleucine, methionine, phenylalanine, threonine, tryptophan, valine, histidine, or arginine) and non-essential amino acids (e.g., serine, asparagine, glutamine, aspartic acid, glutamic acid, alanine, tyrosine, cysteine, glycine, or proline). Non-limiting examples of flavonoids include anthocyanin compounds (e.g., cyanidin-3-glucoside and cyanidin-3-rutino side).

The compositions can include a triglyceride, a preservative, an essential oil, a UV absorption ingredient, and/or additional ingredients described in the specification and known in the art, and any combination thereof. Non-limiting examples of triglycerides include small, medium, and large chain triglycerides. Non-limiting examples of preservatives include methylparaben, propylparaben, or a mixture of methylparaben and propylparaben. Non-limiting examples of essential oils are those described in the specification and those known to a person of ordinary skill in the art. Examples include sesame oil, macadamia nut oil, tea tree oil, evening primrose oil, Spanish sage oil, Spanish rosemary oil, Coriander oil, Thyme oil, or Pimento berries oil. Non limiting examples of UV absorption ingredients include dibenzoylmethane derivatives (e.g., avobenzone), octocrylene, oxybenzone, homosalate, octisalate, octyl methoxycinnamate, ecamsule, titanium dioxide, zinc oxide, etc., and others described in the specification and known to those in the art, and any combination thereof.

In addition to the azuki and navy bean or extracts thereof, the compositions of the present invention can include water, butylene glycol, triethanolamine, and/or a preservative, or any combination thereof. In certain aspects, the compositions can include at least 50, 60, 70, 80, or 90% by weigh of water, 0.5 to 15% by weight of butylene glycol, 0.01 to 3% by weight of triethanolamine, and/or 0.10 to 0.5% by weight of methylparaben. The compositions of the present invention can also include dipotassium glycyrrhizate, ascorbyl glucoside, and/or niacinamide, or any combination thereof. The compositions can include 0.001 to 0.10% by weigh of dipotassium glycyrrhizate, 1.0% to 3.0% by weight of ascorbyl glucoside and/or 0.5% to 1.5% by weight of niacinamide, or any combination thereof. The compositions can also include UV absorbing agents (e.g., homosalate, octisalate, oxybenzone, or avobenzone, or any combination thereof). The amount of UV absorbing agents can range as desired (e.g., 0.00001 to 99%, or any range or integer derivable therein). In particular aspects, the range can be 10% to 20% by weight of a UV absorbing agent or combination of such agents. The compositions of the present can also include glycerin, titanium dioxide, a biosaccharide gum, polyacrylamide, hydrolyzed jojoba esters, and/or propylene glycol, or any combination thereof.

In particular embodiments there is disclosed is a method of lightening skin or evening skin tone comprising applying any one of the compositions of the present invention to the skin. The method can further comprise identify a person in need of lightening skin or evening skin tone. The methods can further include inhibiting melanogenesis in a skin cell, inhibiting tyrosinase or tyrosinase synthesis in a skin cell, or inhibiting melanin transport to keratinocytes in a skin cell. The composition can act as an alpha melanin stimulatory hormone antagonist. The composition can even out pigmentation of the skin. In non-limiting aspect, lightening skin can include reducing the appearance of an age spot, a skin discoloration, or a freckle by topical application of the composition to skin having an age spot, skin discoloration, a freckle, etc.

Also disclosed is a method of treating hyperpigmentation comprising applying any one of the compositions of the present invention to the skin. The method can also comprise identifying a person in need of treating hyperpigmentation. Additional methods contemplated by the inventor include methods for reducing the appearance of an age spot, a skin discoloration, or a freckle, reducing or preventing the appearance of fine lines or wrinkles in skin, or increasing the firmness of skin.

In another embodiment there is disclosed a method of reducing the appearance of uneven skin tone comprising topically applying any one of the compositions of the present invention to skin. The uneven skin tone can be caused by discolored skin. The composition can be applied to discolored skin (e.g., facial skin, arm skin, leg skin, scalp, neck skin, chess skin, abdomen skin, hand skin, etc.). The discolored skin can be an age spot, blotchy skin, a freckle, hyperpigmented skin, skin suffering from melasma, skin that has been over-exposed to sun, etc. The method can also be used to improve a person's skin tone by topical application of the compositions disclosed throughout this specification to skin that has discolored skin. The method can also be used to prevent the appearance of uneven skin tone by topical application of the compositions disclosed throughout this specification to skin that is at risk of developing uneven skin tone. Skin at risk of developing uneven skin tone includes skin that has been over-exposed to sun, pregnant women, people having or at risk of developing melasma, post-inflammatory hyperpigmentation (e.g., darkening of skin after injury to skin such as an acne lesion or a burn). The compositions of the present invention can also be used to lighten skin by topically applying to skin that the user desires to lighten a composition disclosed in this specification.

In broader aspects there is also disclosed is a method of treating or preventing a skin condition comprising topical application of any one of the compositions of the present invention to skin in need thereof. The method can include topical application of the composition to a portion of skin in need of such composition (e.g., skin having a skin condition), wherein topical application reduces or prevents the skin condition when compared to skin that has a skin condition and that has not been treated with the composition. Non-limiting examples of skin conditions include pruritus, spider veins, lentigo, age spots, senile purpura, keratosis, blotches, fine lines or wrinkles, nodules, sun damaged skin, dermatitis (including, but not limited to seborrheic dermatitis, nummular dermatitis, contact dermatitis, atopic dermatitis, exfoliative dermatitis, perioral dermatitis, and stasis dermatitis), psoriasis, folliculitis, rosacea, acne, impetigo, erysipelas, erythrasma, eczema, and other inflammatory skin conditions. In certain non-limiting aspects, the skin condition can be caused by exposure to UV light, age, irradiation, chronic sun exposure, environmental pollutants, air pollution, wind, cold, heat, chemicals, disease pathologies, smoking, or lack of nutrition.

In any of the contemplated treatments, the compositions of the present invention can be applied to facial skin or non-facial skin (e.g., arms, legs, hands, chest, back, feet, etc.). Such methods can further comprise identifying a person in need of skin treatment. The person can be a male or female. The age of the person can be at least 1, 2, 3, 4, 5, 6, 7, 8, 9, 10, 15, 20, 25, 30, 35, 40, 45, 50, 55, 60, 65, 70, 75, 80, 85, 90, 95, or more years old, or any range derivable therein.

The compositions of the present invention can also be used to increase the stratum corneum turnover rate of the skin, increase collagen synthesis in fibroblasts, increase cellular anti-oxidant defense mechanisms (e.g., exogenous additions of anti-oxidants can bolster, replenish, or prevent the loss of cellular antioxidants such as catalase and glutathione in skin cells (e.g., keratinocytes, melanocytes, langerhans cells, etc.) which will reduce or prevent oxidative damage to the skin, cellular, proteins, and lipids), inhibit melanin production in melanocytes, and/or reduce or prevent oxidative damage to skin (including reducing the amount lipid peroxides and/or protein oxidation in the skin). In certain embodiments, compositions of the present invention can decrease the amount of internal oxidation and/or external oxidative damage in a cell. In other aspects, the compositions can increase collagen synthesis in a cell. The compositions can also reduce skin inflammation, such as by reducing inflammatory cytokine production in a cell. Non-limiting examples of such cells include human epidermal keratinocyte, human fibroblast dermal cell, human melanocytes, three dimensional human cell-derived in vitro tissue equivalents comprising human keratinocytes, human fibroblasts, or human melanocytes, or any combination thereof (e.g., combination of human keratinocytes and human fibroblasts or a combination of human keratinocytes and human melanocytes).

Also disclosed is an ingestible composition comprising azuki bean or navy bean or extracts thereof or combinations thereof that can also include and an ingestibly acceptable vehicle.

An injectible solution comprising azuki bean or navy bean or extracts thereof or combinations thereof that can also include an injectibly acceptable solution.

In another aspect, there is disclosed a method of treating or preventing a disease comprising administering to a person in need thereof azuki bean or navy bean or extracts thereof or combinations thereof, wherein the disease is treated or prevented. The disease can be AIDS, an autoimmune disease (e.g., rheumatoid arthritis, multiple sclerosis, diabetes—insulin-dependent and non-independent, systemic lupus erythematosus, or Graves disease), a cancer (e.g., malignant, benign, metastatic, or precancer), a cardiovascular disease (e.g., heart disease, or coronary artery disease, stroke—ischemic and hemorrhagic, or rheumatic heart disease), diseases of the nervous system, an infection by a pathogenic microorganism (e.g., Athlete's Foot, Chickenpox, Common cold, Diarrheal diseases, Flu, Genital herpes, Malaria, Meningitis, Pneumonia, Sinusitis, Skin diseases, Strep throat, Tuberculosis, Urinary tract infections, Vaginal infections, or Viral hepatitis), inflammation (e.g., allergy, or asthma), a prion disease (e.g., CJD, kuru, GSS, or FFI), or obesity.

In a further embodiment there is disclosed a composition comprising azuki bean or navy bean or extracts thereof or combinations thereof. The composition can be included in a topical skin formulation, an injectible composition, an edible composition, or a neutraceutical. The composition can be in the form of an edible pill or gel cap or liquid or powder, or spray or foam or is aerosolized.

In one aspect there is disclosed a method of treating or preventing hair loss comprising administering to a patient in need thereof a composition comprising azuki bean or navy bean or extracts thereof or combinations thereof. The composition can be topically applied to the scalp, eyebrows, or eyelashes. The composition can be in the form of an edible pill or gel cap or liquid or powder and ingested. The composition can be in the form of an injectible solution and is injected. The composition can be in the form of an aerosolized composition or a foam and sprayed onto the scalp, eyebrows, or eyelashes.

In one aspect there is disclosed a method of treating acne, burns, or scars comprising topically applying to acne, a skin burn, or a scar, a composition comprising azuki bean or navy bean or extracts thereof or combinations thereof, wherein the acne, burn, or scar is treated.

Also contemplated is a method of disinfecting skin or a wound comprising topically applying to skin in need of disinfection or to a wound a composition comprising azuki bean or navy bean or extracts thereof or combinations thereof, wherein the skin or wound is disinfected. The wound can be a cut, scrape, abrasion, incision or a burn. The burn can be skin that has been burned by the sun or by another heat source.

Also contemplated are kits that includes the compositions of the present invention. In certain embodiments, the composition is comprised in a container. The container can be a bottle, dispenser, or package. The container can dispense a pre-determined amount of the composition. In certain aspects, the compositions is dispensed in a spray, dollop, or liquid. The container can include indicia on its surface. The indicia can be a word, an abbreviation, a picture, or a symbol.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a foundation, a night cream, a lipstick, a cleanser, a toner, a sunscreen, a mask, or an anti-aging product.

The compositions and methods for their use can "comprise," "consist essentially of," or "consist of" any of the ingredients disclosed throughout the specification. With respect to "consisting essentially of," and in the context of the present invention, this phrase means that it excludes ingredients that materially affect the basic and novel characteristics of a claimed method or stated purpose of a composition. For instances, a composition "consisting essentially of" the claimed ingredients for use in treating uneven skin tone, lightening skin, treating hyperpigmentation, reducing tyrosinase activity, and/or reducing melanogensis excludes ingredients that can negatively affect such treatment methods.

It is contemplated that any embodiment discussed in this specification can be implemented with respect to any method or composition of the invention, and vice versa. Furthermore, compositions of the invention can be used to achieve methods of the invention.

In one embodiment, compositions of the present invention can be pharmaceutically or cosmetically elegant. "Pharmaceutically elegant" and/or "cosmetically elegant" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

"Topical application" means to apply or spread a composition onto the surface of keratinous tissue. "Topical skin composition" includes compositions suitable for topical application on keratinous tissue. Such compositions are typically dermatologically-acceptable in that they do not have undue toxicity, incompatibility, instability, allergic response, and the like, when applied to skin. Topical skin care compositions of the present invention can have a selected viscosity to avoid significant dripping or pooling after application to skin.

"Dermatologically acceptable carrier, vehicle, or medium" means a carrier, vehicle, or medium into which the active ingredients can be effectively incorporated into. A dermatologically acceptable carrier is design to reduce or avoid undue toxicity, incompatibility, instability, allergic response, and the like, when applied to skin.

"Keratinous tissue" includes keratin-containing layers disposed as the outermost protective covering of mammals and includes, but is not limited to, skin, hair and nails.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "treating," "inhibiting," or "reducing" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

Many people in the U.S. and world-wide suffer from hyperpigmentation. This can lead to unwanted freckles or dark spots on the skin which can be aesthetically unpleasant. In many instances, it is often desirable to lighten these discolorations or even out the appearance of the irregularly pigmented areas of skin. Also, in certain cultures, people correlate lighter skin tone or color with beauty. Therefore, people in these cultures may feel the need to lighten their natural skin color with skin-lightening agents or compounds.

Previous attempts to lighten skin or even out skin tone have been made. Combing different types of compounds that have skin lightening properties has also been attempted (e.g., PCT/US99/06794, which is incorporated by reference). The present invention is an effective alternative to the skin-lightening compounds and formulas that are currently used to lighten the skin, treat hyperpigmentation, or other skin tone disorders.

The compositions and methods of the present invention can be used, for example, for improving the skin's visual appearance, whitening or lightening the skin's color or tone, treating hyperpigmentation and other related disorders, and evening out a person's skin tone. The compositions of the present invention can include a combination of ingredients that can be used to lighten skin. Notably, the currently known skin whitening agents and chemicals do not have to be used in a product formulation to achieve skin whitening/lightening benefits in view of the inventor's discovery. These and other non-limiting aspects of the present invention are discussed in further detail in the following sections.

A. Active Ingredients

As explained above, topical skin care compositions of the present invention can include azuki bean and/or navy bean or extracts thereof. The extracts can be obtained with water or alcohol or a combination thereof. Therefore, the extracts can be aqueous extracts, alcoholic extracts, or aqueous/alcoholic extracts. In particular instances, the alcoholic extract is ethanol. Also, the extracts can be in liquid or powdered forms.

With respect to azuki bean extract, the azuki bean is an annual vine (*Vigna angularis* or *Phaseolus angularis*), that produces seeds or beans. It is native in eastern Asian countries ranging from China, Japan, Korea, and Kazakhstan. The bean portion can be used to make extracts of the present invention. Alternatively, azuki bean extract is commercially available from a wide range of sources. For instance, A & E Connock (Perfumery & Cosmetics) Ltd. (United Kingdom) offers a powdered extract that can be used in the context of the present invention under the trade name Adzuki Beans Milled. Further, Carrubba Inc. (Milford, CT USA) produces an aqueous liquid azuki bean extract that can be used in the context of the present invention. The inventors discovered that azuki bean extract has the ability to inhibit/reduce melanogenesis in cells while also reducing tyrosinase activity. The product from Carrubba Inc. was used to procure the results in Example 1 of this application.

As for navy beans and extracts thereof, the navy bean is navy (haricot)-bean (*Phaseolus vulgaris*). *Phaseolus vulgaris* plants produce a wide variety of beans ranging from black turtle beans, cranberry and borlotti beans, flageolet beans, green or yellow pea beans, pink beans, red beans, kidney beans, pinto beans, yellow beans, and navy beans. The current application concerns the navy bean (i.e., navy (haricot) bean (*Phaseolus vulgaris*) and extracts thereof. The navy bean is typically described as a small and oval bean that has an overall neutral or "white" appearance. It is an edible food product that has been described as having a "relatively bland" taste. As illustrated in the Examples, the inventors have discovered that dried milled navy bean powder has surprising skin whitening/lightening properties (see Example 2). It was further discovered that aqueous extracts of this dried milled navy bean powder also exhibit skin whitening/lightening properties (see Example 1). Dried milled navy bean powder is commercially available from a wide range of sources. For the results shown in Example 2, for instance, the powder used was obtained from InfraReady Products (1998) Ltd. (CANADA). For the results shown in Example 1, the aqueous extract was produced from InfraReady's dried milled navy bean powder by Carrubba Inc. (Milford, CT, USA). The extract was produced by running water over the dried powder and collecting the resulting liquid—the liquid was used in Example 1.

In addition to the commercially availability of the extracts identified above, said extracts can be produced by obtaining the corresponding plant or portion thereof (bean) to produce the extract by extraction methods which are known to those of ordinary skill in the art. For instance, a person of ordinary skill in the art would be able to isolate any one of the extracts identified above from the bean by using any suitable method known in the art. In one non-limiting example, the bean is crushed up (e.g., blender) and then subjected to a desired solvent (e.g., water, alcohol, water/alcohol combination) to obtain the desired extract. The extract can then be stored in liquid form, lyophilized, or subject to further processing techniques (e.g., heating, cooling, etc.).

B. Compositions of the Present Invention

It is contemplated that the compositions of the present invention can include azuki bean and/or navy bean or extracts thereof or combinations of both. Additionally, the compositions can include any number of combinations of additional ingredients described throughout this specification. The concentrations of the any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

The disclosed compositions of the present invention may also include various antioxidants to retard oxidation of one or more components. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

C. Vehicles

The compositions of the present invention can be incorporated into all types of cosmetically and dermalogically acceptable vehicles. Non-limiting examples of suitable vehicles include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, and ointments or by other method or any combination of the forgoing as would be known to one of ordinary skill in the art (Remington's, 1990). Variations and other appropriate vehicles will be apparent to the skilled artisan and are appropriate for use in the present invention. In certain aspects, it is important that the concentrations and combinations of the compounds, ingredients, and agents be selected in such a way that the combinations are chemically compatible and do not form complexes which precipitate from the finished product.

It is also contemplated that the azuki bean and/or navy bean or extracts thereof can be individually or combinatorially encapsulated for delivery to a target area such as skin. Non-limiting examples of encapsulation techniques include the use of liposomes, vesicles, and/or nanoparticles (e.g., biodegradable and non-biodegradable colloidal particles comprising polymeric materials in which the ingredient is trapped, encapsulated, and/or absorbed—examples include nanospheres and nanocapsules) that can be used as delivery vehicles to deliver the ingredient to skin (see, e.g., U.S. Pat. Nos. 6,387,398; 6,203,802; 5,411,744; Kreuter 1998).

D. Cosmetic Products and Articles of Manufacture

The composition of the present invention can also be used in many cosmetic products including, but not limited to, sunscreen products, sunless skin tanning products, hair products, finger nail products, moisturizing creams, skin benefit creams and lotions, softeners, day lotions, gels, ointments, foundations, night creams, lipsticks, cleansers, toners, masks, skin-whiteners/brighteners, or other known cosmetic products or applications. Additionally, the cosmetic products can be formulated as leave-on or rinse-off products. In certain aspects, the compositions of the present invention are stand-alone products.

E. Additional Ingredients

In addition to azuki bean and navy bean or extracts thereof, compositions of the present invention can include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraaminobenzoic acid ("PABA") and corresponding PABA derivatives, titanium dioxide, zinc oxide, etc.), essential oils, vitamins (e.g. A, B, C, D, E, and K), trace metals (e.g. zinc, calcium and selenium), anti-irritants (e.g. steroids and non-steroidal anti-inflammatories), botanical extracts (e.g. aloe vera, chamomile, cucumber extract, *Ginkgo biloba*, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, and manitol), exfoliants, waterproofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhizate). Non-limiting examples of some of these ingredients are provided in the following subsections.

a. UV Absorption Agents

UV absorption agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloy trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutyiphenol, and bis-ethylhexyloxyphenol methoxyphenyltriazine, 4-methylbenzylidenecamphor, and isopentyl 4-methoxycinnamate. Non-limiting examples of physical sunblocks include, kaolin, talc, petrolatum and metal oxides (e.g., titanium dioxide and zinc oxide). Compositions of the present invention can have UVA and UVB absorption properties. The compositions can have an sun protection factor (SPF) of 2, 3, 4, 56, 7, 8, 9, 10, 11, 12, 13, 14, 15, 20, 25, 30, 35, 40, 45, 50, 55, 60, 70, 80, 90 or more, or any integer or derivative therein.

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, aloe barbadensis, aloe-barbadensis extract, aloe barbadensis gel, althea officinalis extract, apricot (*Prunus armeniaca*) kernel oil, arginine, arginine aspartate, arnica montana extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamon (*Elettaria cardamomum*) oil, carnauba (*Copernicia cerifera*) wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*)oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, eucalyptus globulus oil, evening primrose (*Oenothera biennis*) oil, fatty acids, geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (*carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, macadamia ternifolia nut oil, maltitol, matricaria (*chamomilla recutita*) oil, methyl glucose sesquistearate, methylsilanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*Mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, poly silicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Michigan. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Michigan.

g. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

h. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene or trihydroxystearin, or a mixture of both.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

i. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

j. Skin Lightening Agents

Non-limiting examples of skin lightening agents that can be used in the context of the present invention include dipotassium glycyrrhizate, ascorbyl glucoside, niacinamide, hydroquinone, or combination thereof.

2. Pharmaceutical Ingredients

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

F. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

A. Example 1—In Vitro Data

Efficacy of azuki bean extract and navy bean extract is summarized in Table 1.

TABLE 1*

| Extract | Melanogenesis Activity | Tyrosinase Activity |
|---|---|---|
| Azuki Bean Extract** | Yes | — |
| Navy Bean Extract*** | Yes | Yes |

*"Yes" in reference to the data in Table 1 indicates that the identified extract is effective in reducing melanogenesis activity and/or tyrosinase activity in such a manner that it can be used in a composition to treat uneven skin tone and hyperpigmentation and can also be used to lighten/whiten skin.
**Azuki Bean Extract was obtained from Carrubba, Inc. (USA). It was an aqueous extract from dried azuki bean powder.
***Navy Bean Extract was obtained from Carrubba, Inc. (USA). It was an aqueous extract in liquid form obtained from dried milled navy bean powder. The dried milled navy bean powder was obtained from InfraReady Products (1998) Ltd (Canada). The extract was produced by running water over the dried powder and collecting the resulting liquid-the liquid was used in Example 1.

Tyrosinase activity assay: In mammalian cells, tyrosinase catalyzes two steps in the multi-step biosynthesis of melanin pigments from tyrosine (and from the polymerization of dopachrome). Tyrosinase is localized in melanocytes and produces melanin (aromatic quinone compounds) that imparts color to skin, hair, and eyes. Purified mushroom tyrosinase (Sigma) was incubated with its substrate L-Dopa (Fisher) in the presence or absence of each of the extracts in Table 1. Pigment formation was evaluated by colorimetric plate reading at 490 nm. The percent inhibition of mushroom tyrosinase activity was calculated compared to non-treated controls to determine the ability of test extracts to inhibit the activity of purified enzyme. Test extract inhibition was compared with that of kojic acid (Sigma).

B16 Melanogenesis Assay: Melanogenesis is the process by which melanocytes produce melanin, a naturally produced pigment that imparts color to skin, hair, and eyes. Inhibiting melanogenesis is beneficial to prevent skin darkening and lighten dark spots associated with aging. This bioassay utilized B16-F1 melanocytes (ATCC), an immortalized mouse melanoma cell line, to analyze the effect of compounds on melanogenesis. The endpoint of this assay is a spectrophotometric measurement of melanin production and cellular viability. B16-F1 melanocytes, were cultivated in standard DMEM growth medium with 10% fetal bovine serum (Mediatech) at 37° C. in 10% $CO_2$, and treated with each of the extracts identified in the specification. Following incubation, melanin secretion was measured by absorbance at 405 nm and cellular viability was quantified.

B. Example 2—In Vivo Data

In vivo testing was performed on the dried milled navy bean powder, which was purchased from InfraReady Products (1998) Ltd. (CANADA). In particular, a 12 week clinical evaluation for improving skin hyperpigmentation was performed by placing 1% w/w of said dried milled navy bean powder into a test vehicle (cream). As a control, the same test vehicle (cream) was used minus the dried milled navy bean powder.

Study Design and Method: Thirty one (31) panelists were enrolled in the study and 30 panelists completed the study: 21 panelists were randomly placed in the treatment group and 9 panelists were randomly placed in the control group. 1 panelist dropped out of the study due to personal reasons. Panelists read and signed an informed consent. This study required three visits to the CCE testing facility over a twelve week period. The visits were as follows: Day 0, weeks 4, 8 and 12. Each study visit was approximately 15 minutes in duration. During these visits, panelists were visually graded by the study investigator for uneven skin tone, discrete pigment and mottled pigment using the "Global Photo Aging Scale" from 0 to 9 (0=none, 9=severe). The visual grading was followed by taking a set of full face photographs using the VISIA CR and Clarity Pro imaging systems. Photographs obtained from Clarity Pro were analyzed for pigmentation parameters such as brightness intensity, pigment variation and contrast. Additionally panelists were instructed on how to use the test product. Panelists were provided with a study diary, usage instructions, the test product, SPF 30 sunscreen and a moisturizer to be used as needed.

Statistical Analyses: All data obtained at weeks 4, 8 and 12 were compared to baseline readings using repeated measures ANOVA on ranks. Statistical significance was considered at p value≤0.05. All data obtained at weeks 4, 8 and 12 from the treatment group were compared to baseline readings obtained from the control group using a T-test.

Visual Grading Results and Conclusions: Visual grading results are provided in Tables 2-4.

TABLE 2

| Treatment Group<br>Mean Percent Improvement from Baseline<br>[Percentage of Panelists Showing Improvement] | | | |
|---|---|---|---|
| Skin Parameters | 4 weeks (N = 20) | 8 weeks (N = 21) | 12 weeks (N = 21) |
| Uneven Skin Tone (overall assessment including dark blotches and pigmentation) | 15%* [60%] | 14%* [62%] | 18%* [62%] |
| Discrete Pigment (age spots, dark spots, freckles) | 7%* [45%] | 20%* [52%] | 21%* [48%] |
| Mottled Pigment (large irregular dark blotches) | NS | NS | 10%* [62%] |

TABLE 2-continued

| Treatment Group<br>Mean Percent Improvement from Baseline<br>[Percentage of Panelists Showing Improvement] | | | |
|---|---|---|---|
| Skin Parameters | 4 weeks (N = 20) | 8 weeks (N = 21) | 12 weeks (N = 21) |

*Statistically significant at 95% confidence interval;
NS = Not Significant.

TABLE 3

| Untreated Group<br>Mean Percent Improvement from Baseline<br>[Percentage of Panelists Showing Improvement] | | | |
|---|---|---|---|
| Skin Parameters | 4 weeks (N = 10) | 8 weeks (N = 9) | 12 weeks (N = 9) |
| Uneven Skin Tone (overall assessment including dark blotches and pigmentation) | 18%* [40%] | NS | NS |
| Discrete Pigment (age spots, dark spots, freckles) | NS | NS | NS |
| Mottled Pigment (large irregular dark blotches) | NS | NS | NS |

*Statistically significant at 95% confidence interval;
NS = Not Significant.

TABLE 4

| Treated and Untreated Group<br>Mean visual grading scores | | | | | | |
|---|---|---|---|---|---|---|
| | 4 weeks | | 8 weeks | | 12 weeks | |
| Skin Parameters | Treated | Untreated | Treated | Untreated | Treated | Untreated |
| Uneven Skin Tone (overall assessment including dark blotches and pigmentation) | 3.20 | 2.80 | 3.33 | 2.56 | 3.19 | 2.56 |
| Discrete Pigment (age spots, dark spots, freckles) | 3.05 | 2.2 | 2.76 | 1.67 | 2.57 | 1.78 |
| Mottled Pigment (large irregular dark blotches) | 3.05 | 2.2 | 2.86* | 1.56* | 2.62 | 2.00 |

*Statistically significant at 95% confidence interval.

The treated group showed significant improvement in uneven skin tone and discrete pigment at weeks 4, 8 and 12 as compared to baseline. The treated group showed significant improvement in mottled pigment at week 12 as compared to baseline. The untreated group showed no significant improvement in mottled and discrete pigment at weeks 4, 8 and 12 as compared to baseline. The untreated group showed significant improvement for uneven skin tone at week 4 as compared to baseline.

Clarity Pro Results and Conclusions: Clarity pro results are provided in Tables 5-7.

TABLE 5

| Treatment Group<br>Mean Percent Improvement from Baseline<br>[Percentage of Panelists Showing Improvement] | | | |
|---|---|---|---|
| Pigmentation Parameters | 4 weeks (N = 20) | 8 weeks (N = 20) | 12 weeks (N = 19) |
| Brightness Intensity (indicates lightening effect) | 3%* [68%] | 6%* [85%] | 6%* [95%] |
| Pigment Variation (Std. deviation of all skin pixels in the brown space) | NS | 6%* [70%] | 8%* [84%] |
| Contrast (Contrast of neighboring skin pixels within a region of interest) | NS | 8%* [70%] | 9%* [80%] |

*Statistically significant at 95% confidence interval;
NS = Not Significant.

TABLE 6

| Untreated Group<br>Mean Percent Improvement from Baseline<br>[Percentage of Panelists Showing Improvement] | | | |
|---|---|---|---|
| Pigmentation Parameters | 4 weeks (N = 9) | 8 weeks (N = 9) | 12 weeks (N = 9) |
| Brightness Intensity (indicates lightening effect) | NS | NS | 5%* [78%] |
| Pigment Variation (Std. deviation of all skin pixels in the brown space) | {2%^} [33%] | 4%* [67%] | 6%* [78%] |
| Contrast (Contrast of neighboring skin pixels within a region of interest) | NS | NS | NS |

*Statistically significant at 95% confidence interval; NS = Not Significant,
^Statistically significant worsening compared to baseline at 95% confidence interval.

TABLE 7

| Treated and Untreated Group<br>Mean values for pigmentation parameters | | | | | | |
|---|---|---|---|---|---|---|
| | 4 weeks (N = 20) | | 8 weeks (N = 20) | | 12 weeks (N = 19) | |
| Skin Parameters | Treated | Untreated | Treated | Untreated | Treated | Untreated |
| Brightness Intensity (indicates lightening effect) | 45.86 | 41.73 | 47.01 | 41.45 | 46.49 | 42.30 |
| Pigment Variation (Std. deviation of all skin pixels in the brown space) | 26.85 | 30.24 | 24.42 | 28.12 | 24.40 | 27.73 |
| Contrast (Contrast of neighboring skin pixels within a region of interest) | 16.59 | 24.16 | 14.96 | 22.87 | 15.37 | 22.71 |

*Statistically significant at 95% confidence interval.

The treated group showed significant improvement for brightness intensity at weeks 4, 8 and 12 weeks as compared to baseline. The treated group showed significant improvement for pigment variation and contrast at weeks 8 and 12 weeks compared to baseline. The untreated group showed significant improvement for brightness intensity at week 12 compared to baseline. The untreated group showed significant improvement for pigment variation at weeks 8 and 12 compared to baseline. The untreated group showed significant worsening for pigment variation at week 4 as compared to baseline. The untreated group showed no significant improvement for pigment contrast at weeks 4, 8 and 12 compared to baseline.

C. Example 3—Testing Compositions

Non-limiting examples of compositions of the present invention are described in Tables 8 and 9. These compositions can be used as vehicles to perform further assays to determine the therapeutic efficacy of the active ingredients in view of the assays listed in Example 4.

TABLE 8*

| Ingredient | % Concentration (by weight) |
|---|---|
| Phase A | |
| Water | q.s. to 100% |
| Xanthum gum | 0.1 |
| M-paraben | 0.15 |
| P-paraben | 0.1 |
| Citric acid | 0.01 |
| Phase B | |
| Cetyl alcohol | 4.0 |
| Glyceryl stearate + PEG 100 | 4.0 |
| Octyl palmitate | 4.0 |
| Dimethicone | 1.0 |
| Tocopheryl acetate | 0.2 |
| Phase C | |
| Active Ingredients** | 1.0 |

*Sprinkle Xanthum gum in water and mix for 10 min. Subsequently, add all ingredients in phase A and heat to 70-75° C. Add all items in phase B to separate beaker and heat to 70-75° C. Mix phases A and B at 70-75° C. Continue mixing and allow composition to cool to 30° C. Subsequently, add phase C ingredient while mixing.
**The active can be azuki bean extract or navy bean extract or a combination of both. Although the total amount of active ingredients in the Table 1 formulation is 1% w/w, it is contemplated that the amount of active ingredients can be increased or decreased as needed, where the water amount can be increased/decreased accordingly (e.g., q.s.).

TABLE 9*

| Ingredient | % Concentration (by weight) |
|---|---|
| Phase A | |
| Water | q.s. to 100% |
| M-paraben | 0.2 |
| P-paraben | 0.1 |
| Na2 EDTA | 0.1 |
| Shea butter | 4.5 |
| Petrolatum | 4.5 |
| Glycerin | 4.0 |
| Propylene Glycol | 2.0 |
| Finsolve TN | 2.0 |
| Phase B | |
| Sepigel 305 | 2.0 |
| Phase C | |
| Active Ingredient(s)** | 1.0 |

*Add ingredients in phase A to beaker and heat to 70-75° C. while mixing. Subsequently, add the phase B ingredient with phase A and cool to 30° C. with mixing. Subsequently, add phase C ingredient while mixing.
**The active can be azuki bean extract or navy bean extract or a combination of both. Although the total amount of active ingredients in the Table 3 formulation is 1% w/w, it is contemplated that the amount of active ingredients can be increased or decreased as needed, where the water amount can be increased/decreased accordingly (e.g., q.s.).

D. Example 4—Determining Efficacy of the Compositions of the Present Invention The efficacy of compositions or active ingredients within a given composition of the present inventions can be determined by methods known to those of ordinary skill in the art. The following are non-limiting procedures that can be used in the context of the present invention. It should be recognized that other testing procedures can be used, including, for example, objective and subjective procedures. The active ingredients (e.g., azuki bean extract or navy bean extract or any combination thereof) can be tested for their skin efficacy by using the composition vehicles identified in Tables 8 and 9.

Skin moisture/hydration can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72C). Three separate impedance readings can be taken on each side of the face, recorded, and averaged. The T5 setting can be used on the impedance meter which averages the impedance values of every five seconds application to the face. Changes can be reported with statistical variance and significance.

Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether a composition is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and are of the replicas covered by wrinkles or fine lines was determined.

The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

In other non-limiting aspects, the efficacy of the compositions of the present invention can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing the compositions and whitening agents of the present invention or with the base alone as a control. Alternatively, an untreated sample of the skin analog can be used as a control.

Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether the product is inducing irritation. The measurements were made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. Skin clarity is defined as L/C where C is chroma and is defined as $(a^2+b^2)^{1/2}$.

All of the compositions and/or methods disclosed and claimed in this specification can be made and executed without undue experimentation in light of the present disclosure. While the compositions and methods of this invention have been described in terms of particular embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method of whitening skin or evening out skin tone, the method comprising topically applying to skin in need of treatment a composition comprising a *Cocos nucifera* oil and an effective amount of an extract of azuki bean, the effective amount being an effective amount of an extract of azuki bean to reduce melanogenesis activity in the skin, wherein topical application of the composition to the skin whitens the skin or evens out the skin tone by reducing melanogenesis activity in the skin.

2. The method of claim 1, wherein the composition is applied to hyperpigmented skin.

3. The method of claim 1, wherein the composition is applied to melasmic skin.

4. The method of claim 1, wherein the composition is applied to an age spot or freckle.

5. The method of claim 1, wherein the composition includes 0.1 to 5 wt. % of the extract of azuki bean.

6. The method of claim 1, wherein the extract of azuki bean is an aqueous extract.

7. The method of claim 1, wherein the composition reduces tyrosinase activity in the skin.

8. The method of claim 1, wherein the composition does not include an ecdysteroid and does not include a flour or a flour phase.

9. The method of claim 1, wherein the composition does not include a bean or extract thereof other than from azuki bean.

10. The method of claim 1, wherein the composition is in liquid form.

11. The method of claim 1, wherein the composition is formulated as an emulsion.

12. The method of claim 10, wherein the emulsion is an oil-in-water emulsion.

13. The method of claim 1, wherein the composition is formulated as a cream or lotion or paste.

14. The method of claim 1, wherein the composition is formulated as a gel.

15. The method of claim 1, wherein the composition is formulated as a mask.

16. The method of claim 1, wherein the composition is an exfoliating composition.

17. The method of claim 15, wherein the composition is an exfoliating mask.

18. The method of claim 1, wherein the composition contains less than 5 wt. % water.

19. The method of claim 1, wherein the composition is a powder.

20. The method of claim 1, wherein the composition is applied to a face.

* * * * *